US012678566B2

(12) United States Patent (10) Patent No.: US 12,678,566 B2
O'Hare et al. (45) Date of Patent: Jul. 14, 2026

(54) DRUG DELIVERY DEVICE MITIGATING DOSE MEASUREMENT ERRORS

(71) Applicant: Sanofi, Paris (FR)

(72) Inventors: Aidan Michael O'Hare, Warwick (GB); Giles Patrick Arnell Sparrow, Lower Brailes (GB)

(73) Assignee: SANOFI, Paris (FR)

( * ) Notice: Subject to any disclaimer, the term of this patent is extended or adjusted under 35 U.S.C. 154(b) by 1075 days.

(21) Appl. No.: 17/773,742

(22) PCT Filed: Nov. 11, 2020

(86) PCT No.: PCT/EP2020/081784
§ 371 (c)(1),
(2) Date: May 2, 2022

(87) PCT Pub. No.: WO2021/094387
PCT Pub. Date: May 20, 2021

(65) Prior Publication Data
US 2022/0379038 A1      Dec. 1, 2022

(30) Foreign Application Priority Data

Nov. 14, 2019    (EP) ..................................... 19306468

(51) Int. Cl.
*A61M 5/315*          (2006.01)
(52) U.S. Cl.
CPC ............................... *A61M 5/31546* (2013.01)
(58) Field of Classification Search
CPC .......... A61M 5/31533; A61M 5/31545; A61M 5/31546; A61M 5/31548; A61M 5/3155
See application file for complete search history.

(56) References Cited

U.S. PATENT DOCUMENTS

| | | | |
|---|---|---|---|
| 5,135,479 A | 8/1992 | Sibalis et al. | |
| 2010/0298895 A1 | 11/2010 | Ghaffari et al. | |
| (Continued) | | | |

FOREIGN PATENT DOCUMENTS

| | | |
|---|---|---|
| CN | 103458945 A | 12/2013 |
| CN | 103781412 A | 5/2014 |
| (Continued) | | |

OTHER PUBLICATIONS

Notice of Reasons for Rejection, Patent Application No. 2022-527954, dated Jan. 21, 2025, pp. 1-10 (with pp. 1-5 being a translation).

(Continued)

*Primary Examiner* — Dung T Ulsh
(74) *Attorney, Agent, or Firm* — Bond, Schoeneck & King, PLLC

(57) ABSTRACT

A drug delivery device, comprising housing comprising one or more bridging contacts; a movable dial located at least partially within the housing and arranged to move relative to the one or more bridging contacts, the movable dial comprising a series of conductive strips on an exterior surface of the movable dial, wherein the one or more bridging contacts selectively connect and disconnect conductive strips of the series of conductive strips as the movable dial moves to provide alternating electrical signals; at least one electronic component configured to: detect the alternating electrical signals; determine whether the alternating electrical signals are indicative of contact between conductive strips of the series of conductive strips and the one or more bridging contacts; and based on the alternating electrical signals, determine a medicament dosage programmed into the drug delivery device.

28 Claims, 7 Drawing Sheets

(56)         References Cited

U.S. PATENT DOCUMENTS

| | | | |
|---|---|---|---|
| 2014/0142512 A1 | 5/2014 | Butler et al. | |
| 2015/0352287 A1 | 12/2015 | Mercer et al. | |
| 2015/0367079 A1 | 12/2015 | Steel et al. | |
| 2019/0314581 A1 | 10/2019 | Boonzaier et al. | |
| 2021/0290841 A1* | 9/2021 | Katuin | A61M 5/24 |

FOREIGN PATENT DOCUMENTS

| | | | |
|---|---|---|---|
| CN | 104958833 A | 10/2015 |
| CN | 105700730 A | 6/2016 |
| CN | 107923766 A | 4/2018 |
| CN | 108463259 A | 8/2018 |
| CN | 109414548 A | 3/2019 |
| CN | 109939301 A | 6/2019 |
| CN | 110099708 A | 8/2019 |
| DE | 19835940 A1 | 2/2000 |
| JP | 2005204493 A | 7/2005 |
| JP | 2014517734 A | 7/2014 |
| JP | 2016506763 A | 3/2016 |
| JP | 2019500142 A | 1/2019 |
| JP | 2019524232 A | 9/2019 |
| TW | 201929914 A | 8/2019 |
| WO | 2000023852 A1 | 4/2000 |
| WO | WO 2013/098421 | 7/2013 |
| WO | 2017016959 A1 | 2/2017 |
| WO | 2019077094 A1 | 4/2019 |

OTHER PUBLICATIONS

Office Action, JP Patent Application No. 2022-527954, dated Aug. 27, 2024, pp. 1-14 (with pp. 1-8 being a translation).

Search Report, CN Patent Application No. 202080078809X, dated Apr. 28, 2025, pp. 1-2.

Second Office Action, CN Patent Application No. 202080078809.X, dated Nov. 27, 2024, pp. 1-17 (with pp. 1-9 being a translation).

International Preliminary Report on Patentability in International Appln. No. PCT/EP2020/081784, mailed on May 27, 2022, 11 pages.

International Search Report and Written Opinion in International Appln. No. PCT/EP2020/081784, mailed on Dec. 11, 2020, 13 pages.

* cited by examiner

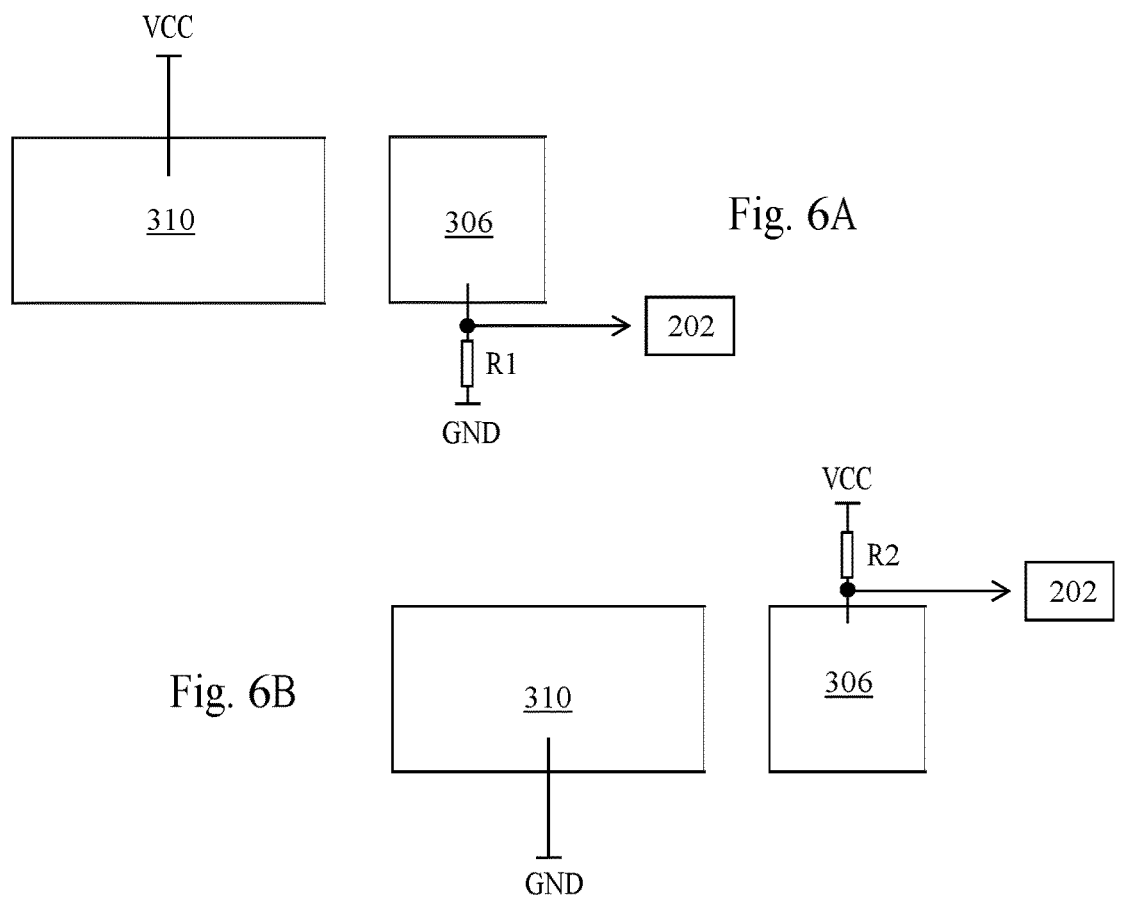
Fig. 6A
Fig. 6B
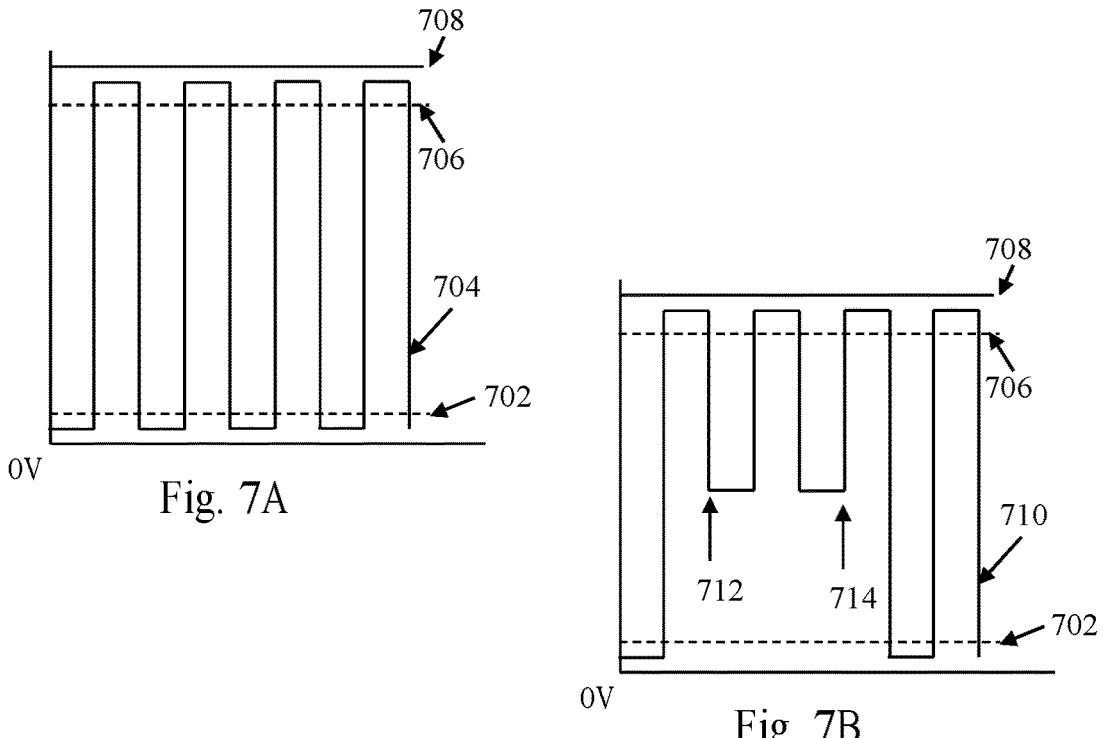
Fig. 7A
Fig. 7B

DRUG DELIVERY DEVICE MITIGATING DOSE MEASUREMENT ERRORS

CROSS REFERENCE TO RELATED APPLICATIONS

The present application is the national stage entry of International Patent Application No. PCT/EP2020/081784, filed on Nov. 11, 2020, and claims priority to Application No. EP 19306468.0, filed on Nov. 14, 2019, the disclosures of which are incorporated herein by reference.

TECHNICAL FIELD

The present disclosure relates to a drug delivery device mitigating dose measurement errors in a drug delivery device, especially an injection device caused by user's body connecting electrical sensor contacts.

BACKGROUND

Pen type drug delivery devices have application where regular injection by persons without formal medical training occurs. This is increasingly common among patients having diabetes where self-treatment enables such patients to conduct effective management of their diabetes.

For good or perfect glycemic control, the dose of insulin or insulin glargine has to be adjusted for each individual in accordance with a blood glucose level to be achieved. The present disclosure relates to injectors, for example hand-held injectors, especially pen-type injectors; that is, the present disclosure relates to injectors of the kind that provide for administration by injection of medicinal products from a multidose cartridge. In particular, the present disclosure relates to such injectors where a user may set the dose. The dose to be injected can for instance be manually selected at the injector by turning a dosage knob and observing the actual dose from a dose window or display of the injector device.

A user undertaking self-administration of insulin will commonly need to administer between 1 and 80 International Units. To be able to monitor dosages, for instance to prevent false handling of the device or to keep track of the doses already applied, it is desirable to measure information related to a condition and/or use of the drug delivery device e.g. the injection device, such as for instance information on the injected dose.

SUMMARY

A drug delivery device is provided, comprising: a housing comprising one or more bridging contacts; a movable dial located at least partially within the housing and arranged to move relative to the one or more bridging contacts, the dial comprising a series of conductive strips on an exterior surface of the dial, wherein the one or more bridging contacts selectively connect and disconnect conductive strips of the series of conductive strips as the movable dial moves to provide alternating electrical signals; at least one electronic component configured to: detect the alternating electrical signals; determine whether the electrical signals are indicative of contact between conductive strips and bridging contact; and based on said electrical signals, determine a medicament dosage programmed into the drug delivery device, especially an injection device.

In one or more embodiments of the drug delivery device, one may utilize one or more of the following features:

the signals are digital signals;

the dial is arranged to rotate relative to the housing and the one or more bridging contacts during a dosage programming event and/or wherein the dial is arranged to helically move out of the housing during a dosage programming event;

wherein the at least one electronic component comprises at least one of the following: microcontroller, a comparator, an analogue to digital converter;

detecting the alternating electrical signal by the at least one electronic component comprises detecting a voltage at at least one of the series of conductive strips;

the at least one electronic component is adapted to compare the voltage detected at the at least one of the series of conductive strips to a threshold voltage;

the at least one electronic component is adapted to compare the analogue voltage detected at the at least one of the series of conductive strips to a threshold voltage;

the at least one electronic component is adapted to increase a dosage count in case the detected voltage is above the threshold voltage;

the at least one electronic component is adapted to not increase a dosage count in case the detected voltage is below the threshold voltage;

the series of conductive strips comprise at least one source strip connected to a battery and at least one sensor strip connected to the at least one electronic component;

the device comprises a microcontroller and wherein the microcontroller has a low-power mode and is configured to wake from the low-power mode upon receiving an electrical signal;

the microcontroller is configured to wake from the low-power mode upon receiving an electrical signal from the electrical connections to the conductive strips;

the device further comprises a resistance element and a switch, the switch selectively connecting the resistance to at least one of the series of conductive strips based on whether the microcontroller is in the low-power mode or not;

the resistance is selectively connected to a sensor strip or strips;

the series of conductive strips comprise at least two sensor strips (306) and at least two source strips;

programming the dose includes dialling the dose;

the series of conductive strips comprise at least one source strip (310) connected to a battery and at least one sensor strip (306) connected to at least one electronic component;

the one or more bridging contacts (304) are not connected to the electronic component, the bridging contacts (304) selectively connecting and disconnecting a source strip (310) to a sensor strip (306) as the movable dial (108) moves to provide alternating electrical signals.

In another aspect a method of operating a drug delivery device is provided, the method comprising: detecting the alternating electrical signals; determining whether the electrical signals are indicative of contact between conductive strips and bridging contact; and based on said electrical signals, determining a medicament dosage programmed into the drug delivery device, especially an injection device.

The method may further comprise: detecting a voltage at at least one of the series of conductive strips, and comparing the voltage detected at the at least one conductive strip to a threshold voltage.

The method may further comprise: in response to determining that the detected voltage is above the threshold voltage, increasing a dosage count in case.

The method may further comprise: in response to determining that the detected voltage is below the threshold voltage, not increasing a dosage count in case the detected voltage is below the threshold voltage.

The method may further comprise: entering, with a microcontroller, a low-power mode; and waking the microcontroller from the low-power mode upon receiving an electrical signal.

The method may further comprise: connecting a resistance to at least one of the series of conductive strips based in response to determining that the microcontroller is in the low-power mode; and disconnecting a resistance element from at least one of the series of conductive strips in response to determining that the microcontroller woke from the low-power mode.

In some embodiments, one or more of the following features could be implemented:

the dial is arranged to rotate relative to the housing and the one or more bridging contacts during a dosage programming event;

the dial is arranged to helically move out of the housing during a dosage programming event;

the conductive strips are arranged to be in electrical contact with the one or more bridging contacts at a first group of relative orientations of the dial and the one or more bridging contacts, and to break the electrical contact with the one or more bridging contacts at a second group of relative orientations of the dial and the one or more bridging contacts, wherein the first group and the second group are different;

the conductive strips are printed, plated or etched on the exterior surface;

the conductive strips are arranged such that the strips comprise source strips which are connected to an electrical potential and sensor strips which comprise an input to the processor;

the source strips and the sensor strips are arranged in an alternating manner around the dial;

the bridging contacts alternately couple source strips to sensor strips, to provide a conductive path between strips, and de-couple electrical contact;

the source strips, the sensor strips and the bridging contacts are arranged to allow a Gray code to be implemented for registering the dialed dose;

the Gray code is a 2-bit Gray code or a 3-bit Gray code;

the dial further comprises a 0U detection strip positioned adjacent to a dose delivery button;

the microcontroller is configured to enter a low-power mode; and wake from the low-power mode upon receiving an electrical signal.

In one embodiment, the drug delivery device comprises an electronic component adapted to detect a voltage detected at at least one of the series of conductive strips, compare the voltage detected at the at least one conductive strip to a threshold voltage, and in case the detected voltage is above the threshold, increase a dosage count; or in case the detected voltage is below the threshold, do not increase a dosage count.

BRIEF DESCRIPTION OF THE FIGURES

The following description is with reference to the following Figures:

4

Figure 1:
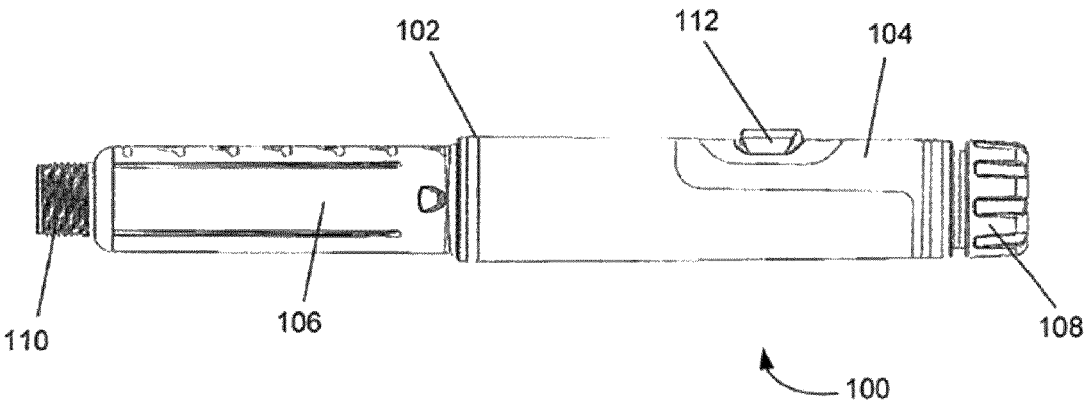
Figure 2:
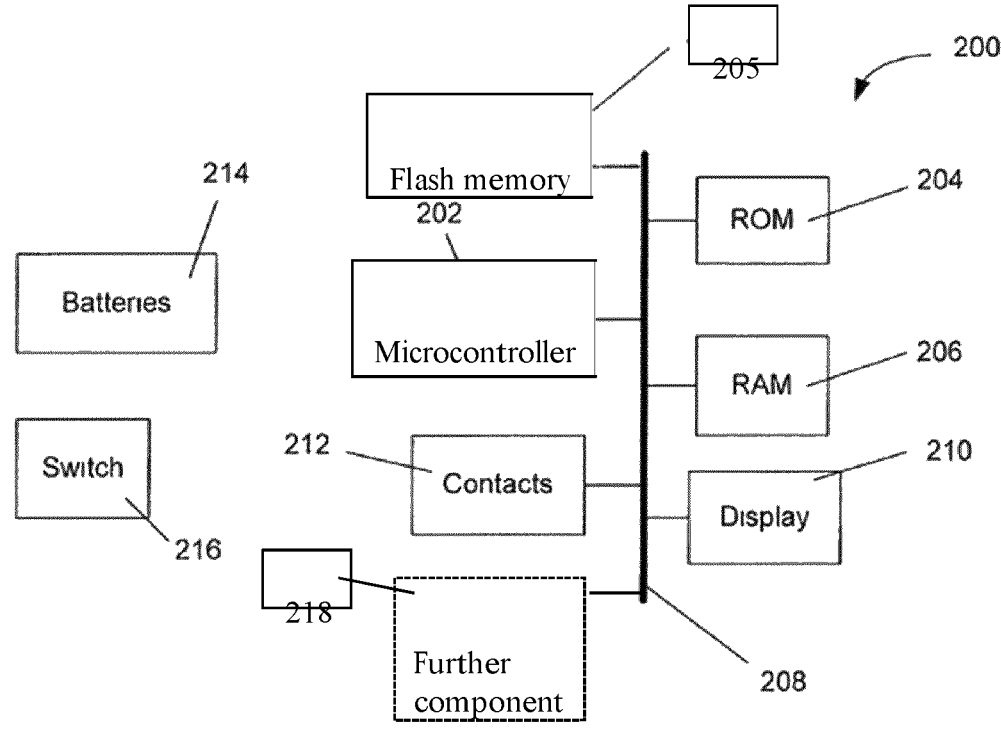
Figures 3A, 3B:
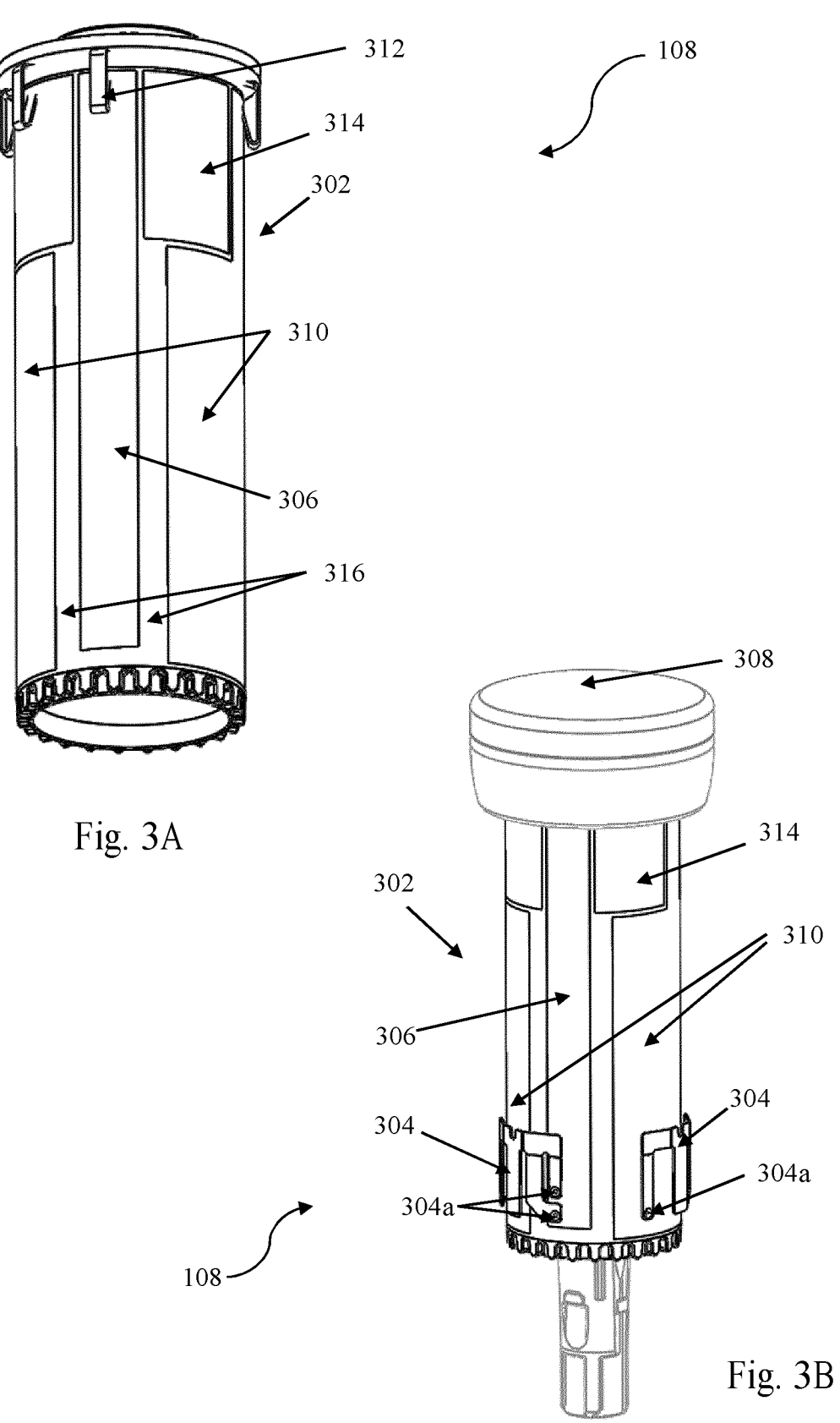
Figure 4A:
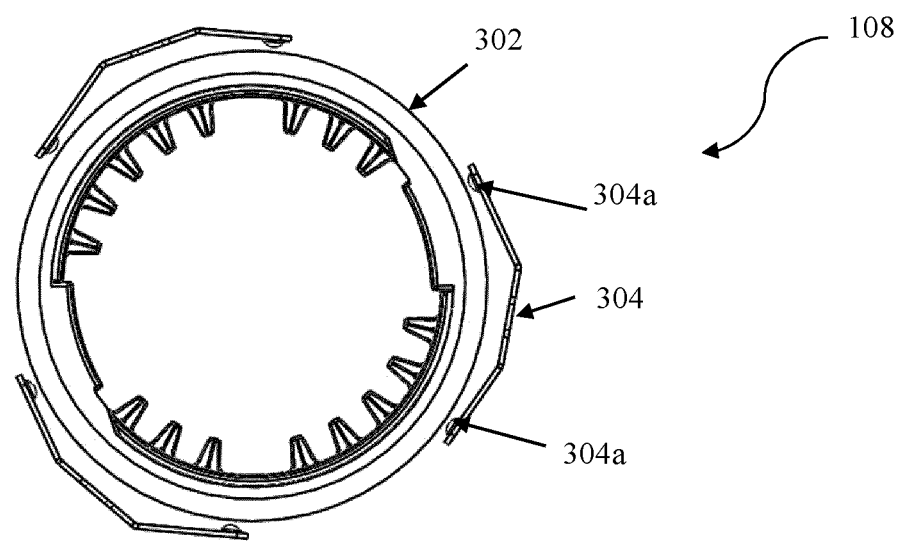
Figure 4B:
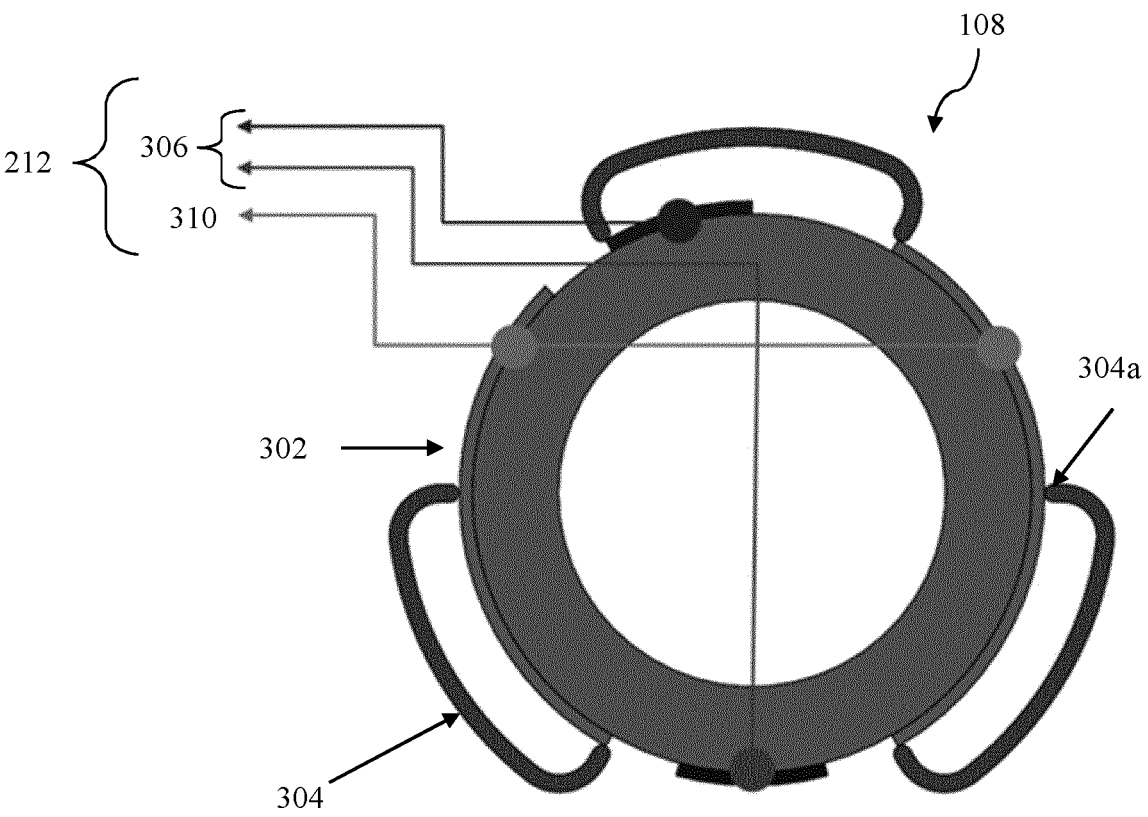
Figure 5A:
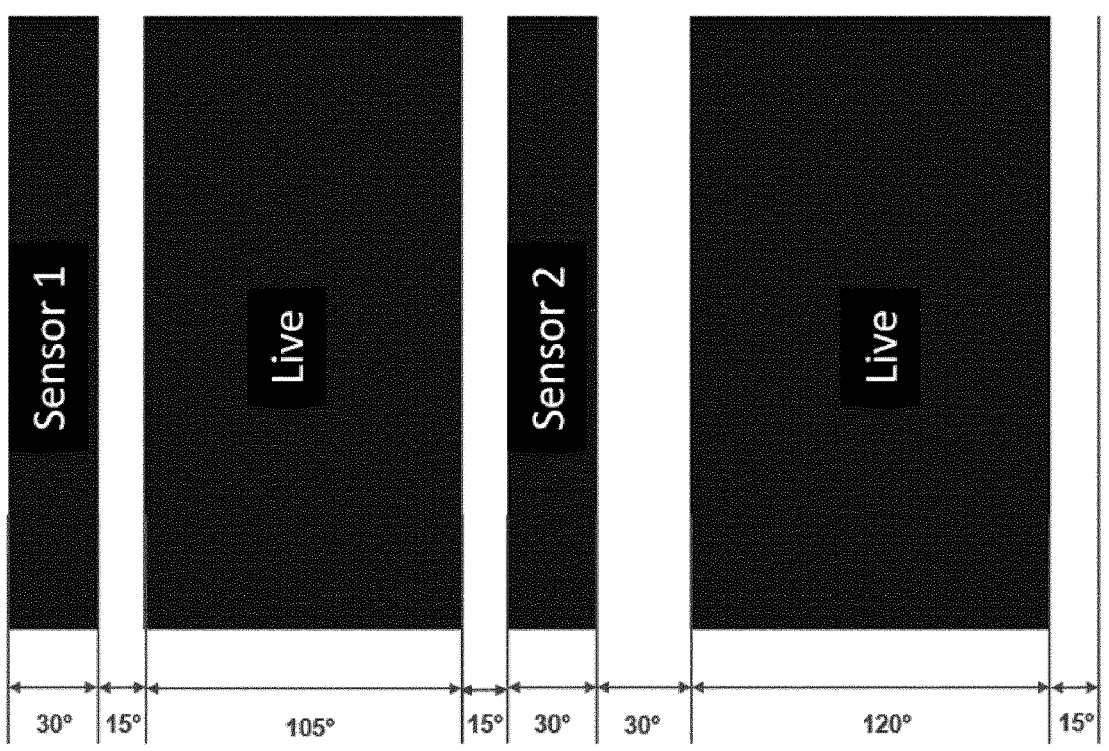
Figure 5B:
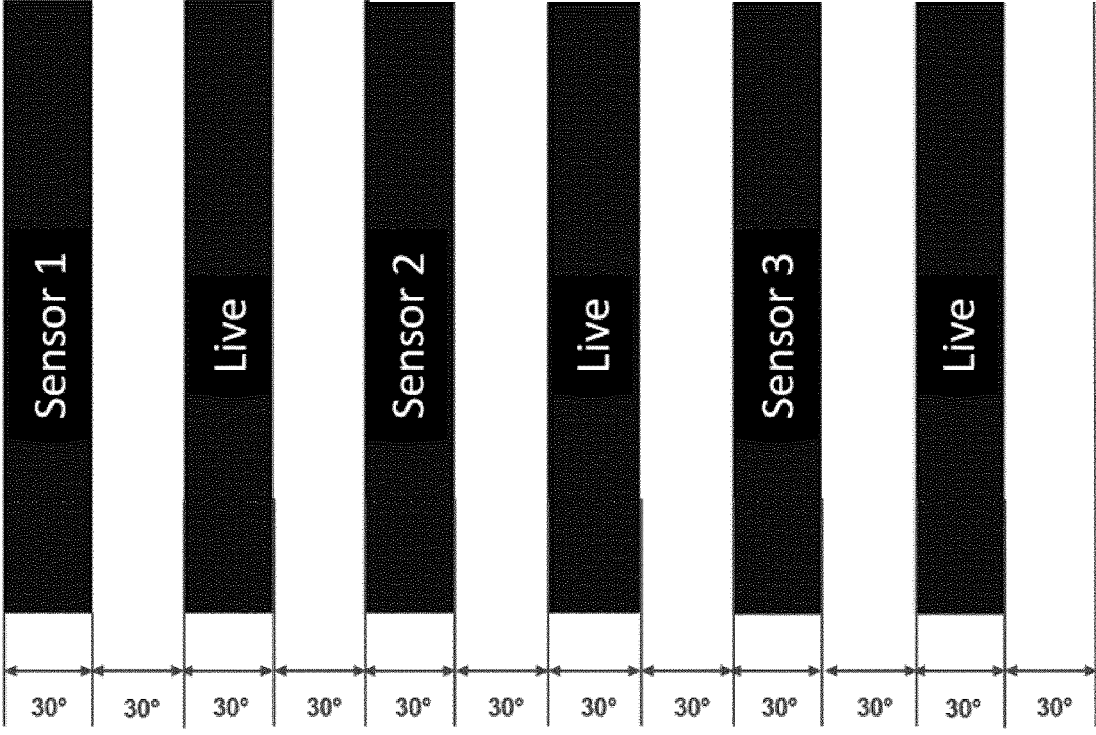
Figure 8:
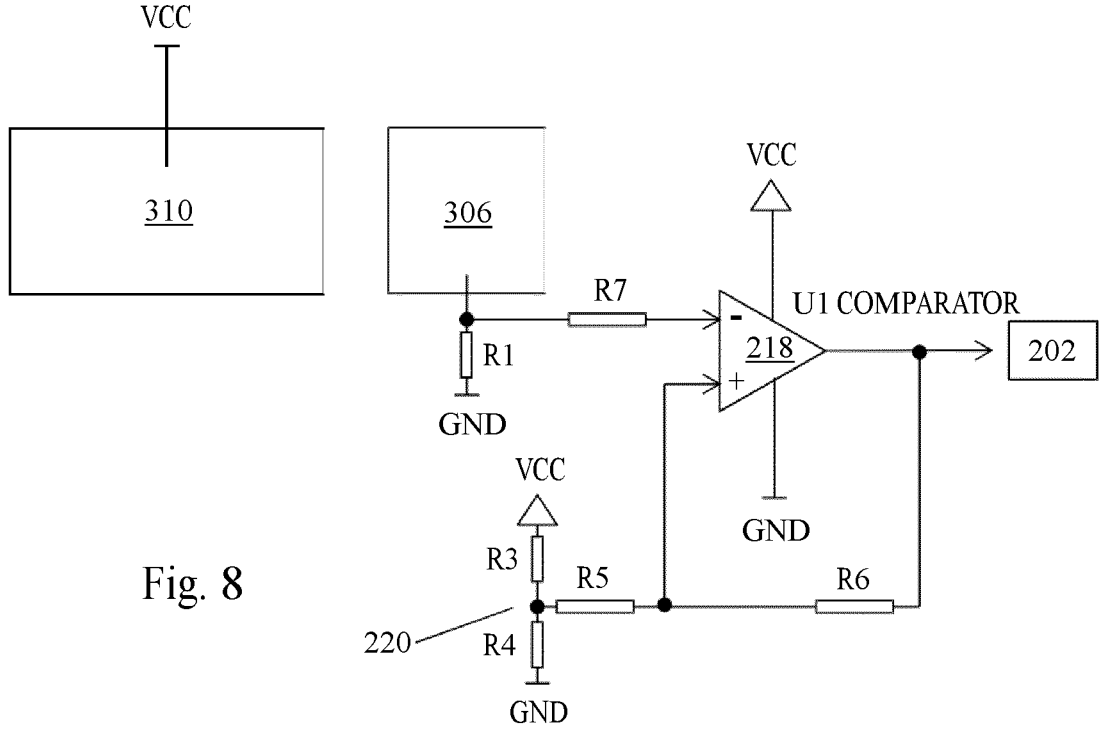
Figure 9:
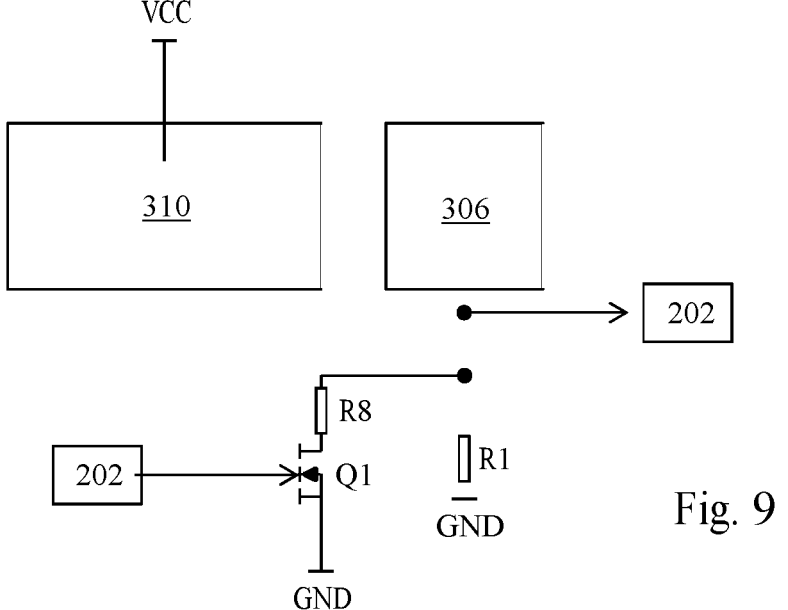
Figure 10:
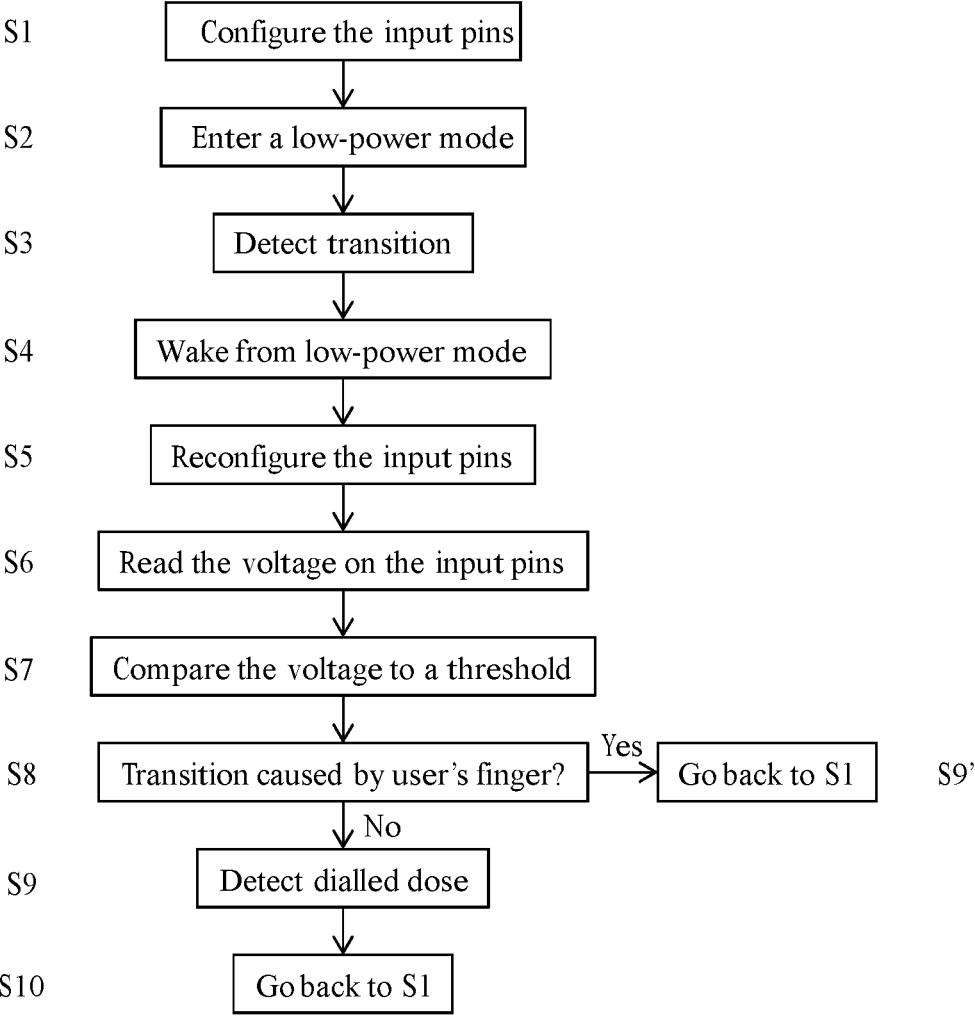

FIG. 1 shows an external view of a drug delivery device 100;

FIG. 2 shows a schematic diagram of some of the electronic components present in the drug delivery device 100 of FIG. 1;

FIGS. 3A and 3B show perspective views of part of a dose setting mechanism 108 of a drug delivery device 100;

FIGS. 4A and 4B show a plan view of part of a dose setting mechanism 108 of a drug delivery device 100;

FIGS. 5A and 5B illustrate example conductive strip arrangements;

FIGS. 6A and 6B show example connections of the conductive strips;

FIGS. 7A and 7B show example signals received from the conductive strips;

FIG. 8 shows an embodiment of circuitry;

FIG. 9 shows an embodiment of circuitry;

FIG. 10 is a flow chart of an example method.

DETAILED DESCRIPTION

Referring firstly to FIG. 1, an external view of a drug delivery device 100 according to embodiments of the disclosure. The device 100 shown in FIG. 1 is a pen type injection device, having an elongate cylindrical shape, for setting and delivering a medicament, such as insulin. The device 100 comprises a housing 102 having a first housing part 104 and a second housing part 106. A rotatable dial 108 is located at a first (or proximal) end of the first housing part 104. The rotatable dial 108 has substantially the same outer diameter as the first housing part 104. The second housing part 106 may be detachably connected to the second end of the first housing part 104. The second housing part 106 is configured to have a needle (not shown) or similar drug delivery apparatus attached to it. To achieve this, the second (or distal) end of the second housing part 106 may have a threaded portion 110. The threaded portion 110 may have a smaller diameter than the remainder of the second housing part 106.

A display mount 112 is located on the first housing part 104. A display may be supported on the display mount 112. The display may be an LCD display, a segmented display or any other suitable type of display. The display mount 112 may cover a recess (not shown) in the first housing portion 104. A number of electronic components, described in greater detail with reference to FIG. 2, may be disposed underneath the display mount 112.

The first housing part 104 contains a drug dose setting and delivery mechanism. The second housing part 106 contains a drug cartridge (not shown). The drug contained in the drug cartridge may be a medicament of any kind and may preferably be in a liquid form. The drug delivery mechanism of the first housing part 104 may be configured to engage with the drug cartridge of the second housing part 106 to facilitate expulsion of the drug. The second housing part 106 may be detached from the first housing part 104 in order to insert a drug cartridge or to remove a used cartridge. The first and second housing parts 104, 106 may be connected together in any suitable way, for example with a screw or bayonet type connection. The first and second housing parts 104, 106 may be non-reversibly connected together in such a way that the drug cartridge is permanently contained within the drug delivery device 100. Further the first and second housing parts 104, 106 may form part of a single housing part.

The rotatable dial 108 is configured to be rotated by hand by a user of the drug delivery device 100 in order to set a drug dose to be delivered. The dial 108 (shown in detail in FIGS. 3A, 3B, 4A, 4B) comprises an internal threading system (not shown) which causes the dial 108 to be displaced axially from the housing 102 as it is rotated in a first direction. The dial 108 may be rotatable in both directions or only in a first direction. Preferably, the dial 108 is rotatable in both directions to allow both increasing (by rotating in the first direction) and decreasing (by rotating in the second direction) the required dose.

The device 100 is configured, once a drug dose has been set by rotation of the rotatable dial 108, to deliver the set drug dose. The set drug dose is delivered for example when a user exerts an axial force at the proximal end of the device. The rotatable dial 108 may support a dose delivery button 308 which is depressed in order to deliver the set drug dose. In an embodiment, the dial 108 does not rotate when the dose delivery button 308 is depressed. When the dose delivery button 308 is depressed, the dial 108 moves towards the body 104 of the device 100 and thus dispenses the drug.

The display 112 may be configured to display information concerning the drug dose which has been set and/or delivered. The display 112 may further show additional information, such as the actual time, the time of the last usage/injection, a remaining battery capacity, one or more warning signs indicating that a dialed dose has not been fully dispensed, and/or the like.

Referring now to FIG. 2, a schematic diagram of an example electrical circuitry 200 forming part of the drug delivery device 100 is shown. The circuitry 200 comprises a microcontroller 202, a non-volatile memory such as a ROM 204, a writable non-volatile memory such as flash memory 205, a volatile memory such as a RAM 206, a display 210, contacts 212 (for example conductive strips 306, 310, described below) and a bus 208 connecting each of these components. The circuitry 200 also comprises batteries 214 or some other suitable source of power for providing power to each of the components and a switch 216, described in greater detail below. The circuitry 200 also comprises a further component 218. In one embodiment, the further component 218 is a comparator. In an embodiment, the further component 218 is an analogue to digital converter (also called AD converter hereinafter).

The circuitry 200 may be integral with the device 100. Alternatively, the circuitry 200 may be contained within an electronic module that can be attached to the device 100. In addition, the circuitry 200 may comprise additional sensors, such as optical or acoustical sensors. The circuitry 200 may comprise an audible alarm (not shown) which the processor 202 may control to sound an alarm when a dialed dose has not been fully dispensed.

The ROM 204 may be configured to store software and/or firmware. This software/firmware may control operations of the processor 202. The processor 202 utilises RAM 206 to execute the software/firmware stored in the ROM to control operation of the display 210. As such the processor 202 may also comprise a display driver. The processor 202 utilises the flash memory 205 to store determined amounts of dose dialed and/or determined amounts of dose dispensed, as will be described in more detail below. The processor 202 may be a microcontroller or microcontroller unit.

The batteries 214 may provide power for each of the components including the contacts 212. The supply of electricity to the contacts 212 may be controlled by the processor 202. The processor 202 may receive signals from the contacts 212. The processor 202 may determine when the contacts 212 are energised, and may be configured to interpret these signals. Information may be provided on the display 210 at suitable times by operation of the software/firmware and the processor 202. This information may include measurements determined from the signals received by the processor 202 from the contacts 212. The electronic module containing circuitry 200 may be embedded within the dial 108. For example, the electronic module may be embedded within the button 308, which can eliminate the requirement to remove and re-use the electronic module when being used in conjunction with a disposable pen injector or other disposable drug delivery device. The embedded electronic module can enable the recording of doses that are dialed and delivered from the pen. This functionality may be of value to a wide variety of device users as a memory aid or to support detailed logging of dose history. It is envisaged that the electronic module could be configured to be connectable to a mobile device, or similar, to enable the dose history to be downloaded from the module on a periodic basis.

An example operation of the dial 108 will now be described with reference to FIGS. 3 to 10. FIGS. 3A and 3B show perspective views of part of a dial 108 of a drug delivery device 100. FIG. 3A shows the dial 108 with the button 308 taken away. FIG. 3B shows the dial 108 with the button 308 in place, and with surrounding components of the body 104 of the device 100. FIGS. 4A and 4B show a plan view of part of a dial 108 of a drug delivery device 100.

The dial 108 comprises a sleeve 302. In an embodiment, the sleeve 302 is cylindrical and is arranged to rotate relative to the first part of the housing 104 during programming of a dosage (but does not rotate relative to the housing 104 during delivery of said dose).

In an embodiment, the sleeve 302 comprises conductive strips 306, 310, 314. The conductive strips may be printed, plated, or etched on an exterior surface of the movable dosage programming component 302 (which exterior surface may be contained within the housing 104 when no dosage is set, as in the arrangement shown in FIG. 1). For example, the conductive strips 306, 310, 314 may be formed from conductive ink. For example, the conductive strips 306, 310, 314 may be formed by electroplating. The resistance of the conductive strips 306, 310, 314, if printed with conductive ink, may be in the range 100Ω-1 kΩ (depending on the ink chosen). In case the conductive strips 306, 310, 314 are electroplated, their resistance may be in the range 0-10Ω.

Some of the conductive strips 306, 310 are live source strips 310, which are electrically connected to a voltage supply to provide an electrical potential. The live source strips 310 may be electrically connected to a voltage supply via a series resistor to limit the current that can flow in this circuit. Other of the conductive strips 306, 310 are sensor strips 306, which electrically connected to input terminals of the processor 202.

The sleeve 302 may comprise at least one source strip 310 and at least one sensor strip 306. In an embodiment, the sleeve 302 comprises more than one of each of source strips 310 and sensor strips 306. For example, the sleeve 302 may comprise two source strips 310 and two sensor strips 306. In principle, the sleeve 302 may comprise any suitable number of conductive strips 306, 310, for example three of each, four of each, five of each, six of each, etc. The sleeve 302 may comprise the same number of each type of conductive strips 306, 310. The source strips 310 may be formed as a continuous strip. The continuous strip may be for example W-shaped (or in a shape of multiple, interconnected U's), with the sensor strips 306 positioned in the gaps formed in the W-shape.

The strips 306, 310 may be positioned such that there is a sensor strip 306 positioned between each two source strips 310 and vice versa. Preferably, the conductive strips 306, 310 are separated by non-conductive gaps 316. Preferably, there is a non-conductive gap between each pair of sensor strip 306 and conductive strip 310. The gaps 316 may be made of the same material as the sleeve 302, e.g. non-conductive plastic. Alternatively, the gaps 316 may be made of a suitable electrically insulating material.

In an embodiment, the sensor strips are electrically connected to the processor 202 embedded in the button 308 by conductive contacts 312. The contacts 312 are positioned within the sleeve 302. The contacts 312 are formed of conductive material, e.g. metal. In an embodiment, one contact 312 is provided per source conductive strip 310 and one contact 312 is provided per sensor conductive strip 306. The number of contacts 312 therefore may correspond to a total number of all conductive strips 306, 310. There may be fewer contacts 312 than the total number of all conductive strips 306, 310 in case the source strips are provided U-shaped, W-shaped or continuously W-shaped, as described above. The contacts 312 may be fixed to the sleeve 302 in such a way to be in permanent contact with the respective adjacent conductive strip 306, 310.

The body 104 of the device 100 comprises bridging contacts 304. The bridging contacts 304 are formed of conductive material, e.g. metal. The bridging contacts 304 are positioned within the body 104 adjacent to the first (proximal) end of the housing 104. The bridging contacts 304 are fixed within the body 104 and are configured to allow a contact between a sensor strip 306 and a source strip 310, between a sensor strip 306 and a gap 316, or between a source strip 310 and a gap 316, depending on turning of the dial 108 and therefore also the sleeve 302. The bridging contacts 304 are not electrically connected to processor 202.

Preferably, each bridging contact 304 has a contact point 304a which is narrower than the gaps 316, to ensure that when the contact point 304a is in contact with any non-conductive gap 316, there is no signal transmitted from the surrounding conductive strips 306, 310.

In one embodiment the bridging contacts 304 are formed using a metal pressing (using stainless steel, for example), with three contact points 304a formed as bumps. This manufacturing approach may facilitate the provision of low cost bridging contacts. The bump contacts 304a are formed at the end of cantilevered members to allow a pre-load to be achieved, ensuring good radial contact pressure with the conductive strips 306, 310 even in worst case tolerance conditions. The bridging contacts 304 may be rotationally and axially aligned within the cylindrical housing 104.

The rotation of the dial 108 is encoded by selectively connecting and disconnecting contacts 212 (the conductive strips 306, 310) on the dosage programming component, thereby alternating electrical signals received by processor 202. Processor 202 may be implemented within any suitable electronic module containing electrical circuitry 200. Turning the dial 108 and thus the sleeve 302 brings the bridging contact into contact with the conductive strips 306, 310. Contact between a sensor strip 306 and a source strip 310 via a bridging contact 304 closes a circuit between the a sensor strip 306 and a source strip 310, the bridging contact 304 and the contacts 312 associated with the respective conductive strips 306, 310. A voltage is thus detected. This may be registered as "1" (logic high). Contact between a source strip 310 or a sensor strip 306 and a gap 316 via a bridging contact 304 breaks the circuit. This may be detected as "0" (logic low).

In this way, using the known positioning of the conductive strips 306, 310 and the gaps 316 turning of the dial 108 and the sleeve 302 relative to the body 104 and the bridging contacts 304 may be detected. The known movement of dial 108 and the sleeve 302 may then be translated into a dialed dose, which may then be stored in a memory and/or displayed and/or transmitted to an external device, as appropriate. Various ways of encoding information may be used; for example, Gray code may be used. For example, the number of conductive strips 306, 310, the width of each conductive strip 306, 310 and the gaps 316 the configuration of the bridging contact etc. may be taken into account to generate a cyclical Gray code during rotation.

FIGS. 3A, B and 4A, B and 5A illustrate an embodiment comprising four vertical conductive strips 306, 310 (two live source strips 310 and two sensor strips 306, alternately arranged), which is suitable for encoding 24 units of dosage. Alternatively or in addition to a code (e.g. numbers) printed on the sleeve 302, the electrical state of the conductive strips 306, 310 themselves may be used to form an input to a microcontroller 202. The rotation of the dial 108 can be encoded electronically to identify the selected dose value before the dose is delivered. The simplest Gray code that can be used to count doses and detect direction of rotation is a 2-bit Gray code. The embodiment shown above uses three bridging contacts 304, spaced equidistant around a circumference of the sleeve 302. In this embodiment, the contact points 304a of the bridging contacts 304 and each extending between two points on the cylinder that are 60° apart.

Other arrangements are possible, as shown in 2D in FIG. 5B. For example, the conductive pattern may have a variable strip width and gap ratio, and in conjunction with the three equi-spaced bridging contacts 304 as described above forms a 2-bit quadrature signal during rotation. The black areas represent regions of conductive material (conductive strips 306, 310), and the white areas represent regions where no conductive material has been deposited (gaps 316. However, there are a number of configurations of conductive strips 306, 310 and bridging contacts 304 that will generate a cyclical Gray code during rotation and so could be used to encode the desired dosage setting.

In general, all the sensor strips 306 may be of the same width, or they may vary in width. Alternatively or in addition, the source strips 310 can be of the same width, or they can vary in width. As apparent from FIG. 5A, one of the gaps 316 may be wider than the remaining gaps. FIG. 5B shows a pattern which can be used to generate a 3-bit Gray code.

The sleeve 302 may further comprise a 0U detection strip 314. The 0U detection strip 314 may be positioned on the sleeve 302 adjacent the dose delivery button 308. During dispensing the dialed dose, the 0U detection strip is normally the last part of the contacts 212 to be brought in contact with the bridging contacts 304. The 0U detection strip 314 may thus be provided to ensure that once the button 308 is pushed all the way down towards the body 104 and the dialed dose is dispensed, this fact is registered as a separate signal. In other words, the 0U detection strip 314 is configured not to be engaged by the bridging contact 314 if the dose is not dispensed or not fully dispensed.

Two embodiments of electronic circuit to be used are shown in FIGS. 6A, 6B. In both embodiments, the source strips 310 are connected to a given electrical potential, as described above. In both embodiments, the electrical potential of the sensor strips 306 is measured and used as an input for the microcontroller 202.

In the embodiment of FIG. 6A, the sensor strips 306 are at low voltage (relative to the battery 214) when not connected by the bridging contacts 304 to the source strips 310. Once a sensor strip 306 is connected by a bridging contact 304 to a source strip 310, the sensor strip 306 is at a potential close to the battery 214. This higher potential is used as an input for the microcontroller 202. In the embodiment of FIG. 6B, a sensor strip is at high voltage (i.e. potential close to the battery potential) when not connected to a source strip 310. Once the sensor strip 306 is connected to the source strip 310 by a bridging contact 304, the potential on the sensor strip 306 is lowered. This lower potential is then used as an input for the microcontroller 202.

The following description is directed to the embodiment of FIG. 6A. It will be apparent to one skilled in the art that the embodiment is applicable to the embodiment of FIG. 6B.

The resistance R1 (see FIG. 6A) ensures that the sensor strip 306 is at a stable potential until connected by the bridging contact 304 to the source strip 310. Preferably, in order to limit the current drawn from the battery, the resistance R1 is as high as possible. For example, the resistance R1 may be in the order of 1 MΩ. The resistance R1 may be e.g. 0.5MΩ-1.5MΩ, 0.8MΩ-1.2MΩ, 0.9MΩ-1.1MΩ, or 1MΩ. A relatively high value of R1, e.g. in the order of 1MΩ, may help in limiting the current flowing into a user who accidentally touches the strips 306, 310, 314.

The resistance of the bridging contact 304 is preferably low, e.g. in the order of 1Ω. The resistance of the bridging contact 304 may be for example 0.5Ω-1.5Ω, 0.8Ω-1.2Ω, 0.9Ω-1.1Ω, 1MΩ. The resistance R1 is thus high compared to the resistance of the bridging contact 304. The voltage on the sensor strip can be therefore read by the microcontroller 202. Such configuration is advantageous because it reduces power consumption and therefore limits the necessary battery size. Preferably, the microcontroller 202 is in a low-power mode whenever the device 100 is not used (i.e. ideally for most of the time) in order to further save the battery. The microcontroller 202 preferably uses the digital signal generated by the change in potential on the sensor strip 306 to wake the microcontroller 202 from the low-power mode without consuming additional power.

Upon rotation of the dial 108, the sleeve 302 extends axially (helically) outwards from the body 104 of the device 100, as described above. This exposes the conductive strips 306, 310. The conductive strips 306, 310 can thus be accidentally connected together by other means than the bridging contacts 304. For example, upon accidentally touching the sleeve 302 and the conductive strips 306, 310, the user may connect the conductive strips 306, 310 by their fingers. If such accidental connection happens in a valid sequence of contacts (i.e. a sequence which could be made by the bridging contacts 304 upon turning the dial 108 and thus setting the dose), such contact may lead to error in recoding of the dialed and/or dispensed dose.

The situation is illustrated in FIGS. 7A and 7B. Preferably, the microcontroller 202 is configured to detect a range of values as "1" (i.e. high potential), and a range of values as "0" (i.e. low potential). This is shown schematically by lines 702 and 706. Any signal that is above the high potential value 706 is detected as high potential, i.e. "1". Any signal that is below the low potential value 702 is detected as low potential, i.e. "0". The area between the lines 702 and 706 is undefined.

FIG. 7A shows a reading in a situation where the dial 108 is turned and no contacts of the conductive strips 306, 310 with user's fingers occurs. As discussed above, the resistance of the bridging contact 304 is low. The potential on the sensor strip 306 where there is no contact between the sensor strip 306 and the source strip 310 via the bridging contact 304 is therefore close to 0V (i.e. below the low potential line 702). The potential on the sensor strip 306 where there is contact between the sensor strip 306 and the source strip 310 via the bridging contact 304 is therefore close to the battery voltage 708 (i.e. above the high potential line 706).

FIG. 7B shows a reading in a situation where the dial 108 is turned and a contact of the conductive strips 306, 310 with user's fingers occurs between points 712 and 714. The contact of the conductive strips 306, 310 with the user's fingers may occur n addition to any circuit formed by the bridging contacts. The resistance of the user's fingers is higher than that of the bridging contacts 304. The influence on the sensor strip 306 when the bridging contact 304 connects the sensor strip 306 and the source strip 310 is negligible. However, the influence on the potential of the sensor strip 306 when the bridging contact 304 does not connect the sensor strip 306 and the source strip 310 is not negligible, and the potential between the points 712 and 714 falls within the undefined region between the lines 702 and 706. This possibly introduces a measurement error in case the undefined value is interpreted as no longer below the low potential line 702 (logic low, "0") and therefore being a high potential value (logic high, "1").

To mitigate the above-described issue, the circuitry 200 is configured to detect potential changes caused by the conductive strips 306, 310 connected by the bridging contacts 304, and reject any potential changes caused by the conductive strips 306, 310 connected by the user's fingers.

In an embodiment, shown in FIG. 8, a comparator 218 is provided. A comparator has two analogue inputs (shown as + and − in FIG. 8) and one digital output. A sensor strip 306 is connected to a first input of the comparator. A second input of the comparator is connected to a constant reference voltage 220. This reference voltage may be set at a value close to the high potential value 706. The digital output of the comparator is logic high ("1") only in case the potential on the sensor strip 306 is higher than the reference value (e.g. above the reference value set to be close to the high potential value 706). Otherwise, the output of the comparator is logic low ("0").

This allows distinguishing the situations shown in FIGS. 7A and 7B. In the situation of FIG. 7A, the output of the comparator is "1" each time. However, in FIG. 7B, the output of the comparator is only "1" outside points 712 and 714, i.e. only when the signal 704 from a sensor strip 306 not only rises above the low potential value 702, but also above the high potential value 706. In general, the tolerance of a comparator can be much smaller than the width of the undefined region between the lines 702 and 706. In addition, because it is possible to set the reference value, the comparator allows higher flexibility (compared e.g. to embodiments in which the low/high potential values 702, 706 are properties of a particular microcontroller used).

In case of a 2-bit rotational encoder (i.e. a sleeve 302 with two sensor strips 306, two source strips 310 and a 0U strip 314, as described above), it is preferred to use three comparators, one per each of the inputs to the microcontroller 202. A first and a second comparator are associated with the two encoder lines (sensor strips 306 and source strips 310) and a third comparator is associated with the 0U strip 314. This arrangement is beneficial in mitigating the risk of connecting the respective sensor strips 306, source strips 310 or 0U strip 314 with the user's fingers.

A further advantage of a comparator as described is its digital output, which may be used as a digital input and a wake-up signal for the microcontroller 202 in case the microcontroller 202 is in a low-power mode.

In an embodiment, an AD converter (not shown) may be used instead of the comparator. The AD converter may be used to convert the sensor strip 306 voltage from an analogue signal to a digital signal. The digital signal may be then compared to a software-set threshold. In this way, the AD converter replicates the behaviour of an external electronic comparator in software. Since many microcontrollers contain embedded AD converters, this arrangement eliminates a need for additional components, such as an additional integrated circuit implementing the comparator of the embodiment described above. This solution is therefore especially suitable for devices in which cost is an issue.

To reduce the power consumption of a continuously running (reading) AD converter and therefore the necessary battery size, the following method may be implemented. An example implementation of the method is illustrated in FIG. 10.

By reconfiguring the pins of the microcontroller 202, the signal (voltage) from the sensor strip 306 the can be configured as a digital input to wake the microcontroller from the low-power mode. A contact between the source strip 310, the sensor strip 306 and the user's finger(s) may cause a transition to be detected that causes the microcontroller to leave the low-power mode. Subsequently, the signal may be read by the AD converter to determine whether the voltage is above threshold (e.g. the high potential value 706) and thus whether the signal corresponds to the source strip 310 and the sensor strip 306 being connected by a bridging contact 304 or by the user's finger(s).

In particular, before entering a low-power mode, the microcontroller 202 (which preferably comprises an embedded AD converter) may configure the input pin connected to each of the two sensor strips 306 and the 0U strip 314 (not shown) as a digital input with an interrupt to wake the microcontroller on a logic level transition (step S1). The microcontroller may then enter a low-power mode (step S2). Thus, when the transition is detected on the sensor strip 306 and/or 0U strip 314 input pin, the microcontroller 202 wakes from the low-power mode (step S3). The microcontroller 202 may then reconfigure the input pin connected to each of the three sensor strips 306 as an analogue input (step S4). The voltage on the input pins corresponding to the sensor strips 306 and/or the 0U strip 314 may be read using the AD converter (step S5). The obtained voltage may be compared to the software-set threshold (step S6). The microcontroller 202 may therefore determine whether the transition was caused by the source strip 310 and the sensor strip 306 and/or the 0U strip 314 being connected by the bridging contact 304 (step S8). In case the transition is determined not to have been caused by the source strip 310 and the sensor strip 306 and/or the 0U strip 314 being connected by the bridging contact 304, the microcontroller 202 may wait for a suitable delay, return to configuring the input pin connected to each of the two sensor strips 306 and the 0U strip 314 (not shown) as a digital input with an interrupt to wake the microcontroller on a logic level transition, and continue the above-described sequence of steps (step S9'). In case the transition is determined to have been caused by the source strip 310 and the sensor strip 306 and/or the 0U strip 314 being connected by the bridging contact 304, the microcontroller 202 may increment or decrement the current count of dose selected (step S9). It may then then continue to poll the analogue voltage on the input pins corresponding to the sensor strips 306 and/or the 0U strip 314 and record the dialed dose, until no activity is detected for a suitable delay and the microcontroller returns to the first step in this sequence, i.e. step S1 (step S10).

As discussed above, it is advantageous from the battery life point of view to have the value of resistance R1 as high as possible, and in particular significantly higher compared to the resistance of the bridging contact 304. However, the lower the resistance R1, the lower the value of resistance bridging the source and sensor strips that causes a measurement error.

To address this issue, in an embodiment (which can be combined with any of the embodiments described above), the arrangement of FIG. 9 may be employed. The circuitry shown in FIG. 9 includes an additional resistance element R8. The resistance element can be for example a resistor. The value of the resistance of the resistance element R8 is low compared to the resistance R1. For example, the value of resistance R8 may be in the order of 100 kΩ. For example, the value of resistance R8 may be less than 200 kΩ, less than 180 kΩ, or less than 170 kΩ. For example, the value of resistance R8 may be 164 kΩ. In general, the value of R8 is selected such that it is sufficiently low compared to the resistance R1 (discussed above), but sufficiently high so that it complies with any given safety limits limiting the current possibly flowing through the user's fingers if the user accidentally touches the contacts.

The resistance R8 is provided in parallel with the resistance R1. Q1 is a switch operated by the microcontroller 202. The switch Q1 can be e.g. a transistor. When the microcontroller 202 is in a low-power mode, the switch Q1 is open. The resistance connected to the sensor strip 306 is thus high (for example in the order of 1MΩ; the possible values of R1 are discussed above). When the microcontroller 202 wakes from the low-power mode, the microcontroller 202 closes the switch Q1. The effective value of resistance is reduced from R1 to the parallel combination of R1 and R8, thus making the circuit tolerant to less resistive fingers bridging the source and sensor strips.

Providing the arrangement of FIG. 9 may help saving battery life. Because the microcontroller 202 is expected to be in the low-power state for the majority of its life, this switching of resistance between R1 and the parallel combination of R1 and R8 may have only an insignificant impact on battery life.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids.

Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetrade-canoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspo-glutide, Albiglutide (Syncria®), Dulaglutide (Trulicity®), rExendin-4, CJC-1134-PC, PB-1023, TTP-054, Lan-glenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An examples of an oligonucleotide is, for example: mipomersen sodium (Kynamro®), a cholesterol-reducing antisense therapeutic for the treatment of familial hypercho-lesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutro-pin, Choriongonadotropin, Menotropin), Somatropine (So-matropin), Desmopressin, Terlipressin, Gonadorelin, Trip-torelin, Leuprorelin, Buserelin, Nafarelin, and Goserelin.

Examples of polysaccharides include a glucosaminogly-cane, a hyaluronic acid, a heparin, a low molecular weight heparin or an ultra-low molecular weight heparin or a derivative thereof, or a sulphated polysaccharide, e.g. a poly-sulphated form of the above-mentioned polysaccha-rides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immu-noglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

The invention claimed is:

1. A drug delivery device, comprising:
a housing comprising one or more bridging contacts;
a movable dial located at least partially within the housing and arranged to move relative to the one or more bridging contacts, the movable dial comprising a series of conductive strips on an exterior surface of the movable dial, wherein the one or more bridging contacts selectively connect and disconnect conductive strips of the series of conductive strips as the movable dial moves to provide alternating electrical signals; and
at least one electronic component configured to:
    detect the alternating electrical signals, wherein the signals are digital signals,
    determine whether the alternating electrical signals are indicative of contact between conductive strips of the series of conductive strips and the one or more bridging contacts, and
    based on the alternating electrical signals, determine a medicament dosage programmed into the drug delivery device.

2. The drug delivery device of claim 1, wherein the movable dial is arranged to rotate relative to the housing and the one or more bridging contacts during a dosage programming event, or wherein the movable dial is arranged to helically move out of the housing during the dosage programming event.

3. A drug delivery device, comprising:
a housing comprising one or more bridging contacts;
a movable dial located at least partially within the housing and arranged to move relative to the one or more bridging contacts, the movable dial comprising a series of conductive strips on an exterior surface of the movable dial, wherein the one or more bridging contacts selectively connect and disconnect conductive strips of the series of conductive strips as the movable dial moves to provide alternating electrical signals; and
at least one electronic component configured to:
    detect the alternating electrical signals,
    determine whether the alternating electrical signals are indicative of contact between conductive strips of the series of conductive strips and the one or more bridging contacts, and
    based on the alternating electrical signals, determine a medicament dosage programmed into the drug delivery device,
wherein the at least one electronic component comprises at least one of a microcontroller, a comparator, and an analogue to digital converter.

4. A drug delivery device, comprising:
a housing comprising one or more bridging contacts;
a movable dial located at least partially within the housing and arranged to move relative to the one or more bridging contacts, the movable dial comprising a series of conductive strips on an exterior surface of the movable dial, wherein the one or more bridging contacts selectively connect and disconnect conductive strips of the series of conductive strips as the movable dial moves to provide alternating electrical signals; and
at least one electronic component configured to:
    detect the alternating electrical signals,
    determine whether the alternating electrical signals are indicative of contact between conductive strips of the series of conductive strips and the one or more bridging contacts, and
    based on the alternating electrical signals, determine a medicament dosage programmed into the drug delivery device, wherein detecting the alternating electrical signal by the at least one electronic component comprises detecting a voltage at at least one of the series of conductive strips.

5. The drug delivery device of claim 4, wherein the at least one electronic component is adapted to compare the voltage detected at the at least one of the series of conductive strips to a threshold voltage.

6. The drug delivery device of claim 4, wherein the at least one electronic component is adapted to compare the analogue voltage detected at the at least one of the series of conductive strips to a threshold voltage.

7. The drug delivery device of claim 5, wherein the at least one electronic component is adapted to increase a dosage count in case the detected voltage is above the threshold voltage.

8. The drug delivery device of claim 4, wherein the at least one electronic component is adapted to not increase a dosage count in case the detected voltage is below the threshold voltage.

9. The drug delivery device of claim 1, wherein the series of conductive strips comprises at least one source strip connected to a battery and at least one sensor strip connected to the at least one electronic component.

10. The drug delivery device of claim 9, wherein the device comprises a microcontroller, and wherein the microcontroller has a low-power mode and is configured to wake from the low-power mode upon receiving an electrical signal.

11. The drug delivery device of claim 10, wherein the microcontroller is configured to wake from the low-power mode upon receiving the electrical signal from electrical connections to the series of conductive strips.

12. The drug delivery device of claim 10, further comprising a resistance element and a switch, the switch selectively connecting the resistance element to at least one of the series of conductive strips based on whether the microcontroller is in the low-power mode or not.

13. The drug delivery device of claim 12, wherein the resistance element is selectively connected to one or more sensor strips.

14. A drug delivery device, comprising:
a housing comprising one or more bridging contacts;
a movable dial located at least partially within the housing and arranged to move relative to the one or more bridging contacts, the movable dial comprising a series of conductive strips on an exterior surface of the movable dial, wherein the one or more bridging contacts selectively connect and disconnect conductive strips of the series of conductive strips as the movable dial moves to provide alternating electrical signals; and
at least one electronic component configured to:
detect the alternating electrical signals,
determine whether the alternating electrical signals are indicative of contact between conductive strips of the series of conductive strips and the one or more bridging contacts, and
based on the alternating electrical signals, determine a medicament dosage programmed into the drug delivery device,
wherein the series of conductive strips comprise at least two sensor strips and at least two source strips.

15. The drug delivery device of claim 1, wherein programming the dose includes dialing the dose.

16. The drug delivery device of claim 1, wherein the one or more bridging contacts are not connected to the at least one electronic component, the one or more bridging contacts selectively connecting and disconnecting a source strip to a sensor strip as the movable dial moves to provide the alternating electrical signals.

17. A method of operating a drug delivery device, the drug delivery device comprising:
a housing comprising one or more bridging contacts,
a movable dial located at least partially within the housing and arranged to move relative to the one or more bridging contacts, the movable dial comprising a series of conductive strips on an exterior surface of the movable dial, wherein the one or more bridging contacts selectively connect and disconnect conductive strips of the series of conductive strips as the movable dial moves to provide alternating electrical signals, and
at least one electronic component, the method comprising:
detecting the alternating electrical signals, wherein the signals are digital signals;
determining whether the alternating electrical signals are indicative of contact between conductive strips of the series of conductive strips and the one or more bridging contacts; and
based on the alternating electrical signals, determining a medicament dosage programmed into the drug delivery device.

18. The method of claim 17, further comprising:
detecting a voltage at at least one of the series of conductive strips; and
comparing the voltage detected at the at least one conductive strip to a threshold voltage.

19. The method of claim 18, further comprising:
in response to determining that the voltage is above the threshold voltage, increasing a dosage count in case.

20. The method of claim 19, further comprising:
in response to determining that the voltage is below the threshold voltage, not increasing a dosage count in case the voltage is below the threshold voltage.

21. The method of claim 17, further comprising:
entering, with a microcontroller, a low-power mode; and
waking the microcontroller from the low-power mode upon receiving an electrical signal.

22. The method of claim 21, further comprising:
connecting a resistance element to at least one of the series of conductive strips in response to determining that the microcontroller is in the low-power mode; and
disconnecting the resistance element from at the least one of the series of conductive strips in response to determining that the microcontroller woke from the low-power mode.

23. The drug delivery device of claim 3, wherein the one or more bridging contacts are not connected to the at least one electronic component, the one or more bridging contacts selectively connecting and disconnecting a source strip to a sensor strip as the movable dial moves to provide the alternating electrical signals.

24. The drug delivery device of claim 3, wherein the series of conductive strips comprises at least one source strip connected to a battery and at least one sensor strip connected to the at least one electronic component.

25. The drug delivery device of claim 4, wherein the one or more bridging contacts are not connected to the at least one electronic component, the one or more bridging contacts selectively connecting and disconnecting a source strip to a sensor strip as the movable dial moves to provide the alternating electrical signals.

26. The drug delivery device of claim 4, wherein the series of conductive strips comprises at least one source strip connected to a battery and at least one sensor strip connected to the at least one electronic component.

27. The drug delivery device of claim 14, wherein the signals are digital signals.

28. A method of operating a drug delivery device, the drug delivery device comprising:

a housing comprising one or more bridging contacts;

a movable dial located at least partially within the housing and arranged to move relative to the one or more bridging contacts, the movable dial comprising a series of conductive strips on an exterior surface of the movable dial, wherein the one or more bridging contacts selectively connect and disconnect conductive strips of the series of conductive strips as the movable dial moves to provide alternating electrical signals; and at least one electronic component, the method comprising:

detecting the alternating electrical signals by detecting a voltage at at least one of the series of conductive strips, determining whether the alternating electrical signals are indicative of contact between conductive strips of the series of conductive strips and the one or more bridging contacts, and based on the alternating electrical signals, determining a medicament dosage programmed into the drug delivery device.

* * * * *